United States Patent [19]
Sakamoto et al.

[11] Patent Number: 5,971,929
[45] Date of Patent: Oct. 26, 1999

[54] STOPPER MECHANISM FOR ENDOSCOPICALLY INSERTING ULTRASOUND PROBE

[75] Inventors: Toshio Sakamoto; Toshizumi Tanaka; Hiromu Itoi; Masatoshi Yoshihara, all of Omiya, Japan

[73] Assignee: Fuji Photo Optical Co., Ltd., Omiya, Japan

[21] Appl. No.: 09/152,791

[22] Filed: Sep. 14, 1998

[51] Int. Cl.[6] ........................................................ A61B 8/00
[52] U.S. Cl. .............................................................. 600/462
[58] Field of Search ................................... 600/462, 459, 600/461, 466, 467

[56] References Cited

U.S. PATENT DOCUMENTS

| | | | |
|---|---|---|---|
| 5,464,016 | 11/1995 | Nicholas et al. | 600/466 |
| 5,596,991 | 1/1997 | Tanaka | 600/459 |
| 5,827,175 | 10/1998 | Tanaka | 600/459 |

*Primary Examiner*—William E. Kamm
*Assistant Examiner*—Maulin Patel
*Attorney, Agent, or Firm*—Oblon, Spivak, McClelland, Maier & Neustadt, P.C.

[57] ABSTRACT

A stopper mechanism for an endoscopically insertable ultrasound probe which is designed to be introduced into a body cavity through a biopsy channel provided internally of an insertion instrument of an endoscope and which is of the type having a bulky ultrasound scanner head at the distal end of an elongated thin flexible cord and being placed in the endoscopic biopsy channel except the bulky scanner head when in use. A stopper protuberance is projected radially outward from a connecting neck portion of the ultrasound probe immediately on the proximal side of the scanner head where the flexible cord of the ultrasound probe is connected to a connecting member axially extended from the ultrasound scanner head. The stopper protuberance is abutted against marginal edges of a front opening of the endoscopic biopsy channel at a distal end of the endoscopic insertion instrument prior to the scanner head when the flexible cord is pulled thereinto, thereby keeping the scanner head from loads which would be imposed thereon upon direct abutment against a distal end portion of the endoscopic insertion instrument. The stopper protuberance can be realized in various forms, including an annular protuberance formed on the circumference of an outer tube of the flexible cord or of the connecting member in the connecting neck portion, and a wedge ring fitted on a fore end portion of the outer tube.

5 Claims, 13 Drawing Sheets

STOPPER MECHANISM FOR ENDOSCOPICALLY INSERTING ULTRASOUND PROBE

FIELD OF THE ART

This invention relates generally to an ultrasound examination system employing an endoscopically insertable ultrasound probe to be introduced into a body cavity through a biopsy channel within an endoscopic insertion instrument, and more particularly to an endoscopically inserting ultrasound probe with a stopper mechanism for fixedly holding an ultrasound scanner head at the distal end of an endoscopic insertion instrument without exerting a force on the scanner head itself.

PRIOR ART

Regarding ultrasound examination systems in use for acquiring information on intracorporeal tissues, it has been known to introduce an endoscopically inserting ultrasound probe into a body cavity through an endoscopic instrument channel or a biopsy channel which is provided within an endoscopic insertion instrument. An ultrasound examination system of this sort is largely constituted by an ultrasound probe, a probe controller and an ultrasound image observation terminal. For making ultrasound scans, the ultrasound probe is provided with an ultrasound scanner head at the tip end of a flexible cord. The ultrasound scanner head has an ultrasound transducer element housed in an end cap fixedly attached to the tip end of the flexible cord. The probe controller serves to control the operations of the ultrasound transducer element, and the ultrasound image observation terminal includes an ultrasound driver which drives the ultrasound transducer element for transmission of ultrasound pulses, along with a signal processor for processing received ultrasound echo signals into ultrasound images to be displayed on a monitor screen.

For placement in an endoscopic biopsy channel, a major part of the ultrasound probe is constituted by a flexible cord of a smaller diameter as compared with the inside diameter of the endoscopic biopsy channel. In an ultrasound scanning operation, while transmitting ultrasound pulse signals toward an intracorporeal portion of interest at predetermined intervals, return echoes are received and converted into electrical signals through the ultrasound transducer element to acquire information of intracorporeal tissues over a predetermined range. The ultrasound transducer element is scanned in a linear direction in a linear ultrasound scanning operation and in a radial or rotational direction in a radial ultrasound scanning operation. For a radial scan, the ultrasound transducer element needs to undergo rotation by means of a motor or other rotational drive means, which however is too bulky to be provided at the distal end of the ultrasound probe. Therefore, it is the usual practice to provide on the ultrasound probe a rotation transmission means, which permits to remote-control the rotation of the ultrasound transducer element, in cooperation with a rotational drive means and rotational angle detection means which are provided on the part of the probe controller of the ultrasound examination system. For this purpose, the probe controller may be provided separately from an ultrasound image observation terminal, or, if desired, may be assembled into an ultrasound image observation terminal as an integral part thereof.

As the rotation transmission means, it has been the general practice to provide on the ultrasound probe a flexible shaft which is connected to the ultrasound transducer element at its fore end. The flexible shaft of this sort is usually in the form of a hollow coil tube consisting of layers of tightly wound coils and internally providing a passage for a cable to be connected to the ultrasound transducer element. The flexible shaft is fitted in a flexible sheathing tube and is rotatable therein to transmit its rotation to the distal end of the probe to rotate the ultrasound transducer element.

The ultrasound probe is provided with a connector at its proximal end for disconnectibly coupling same with the ultrasound controller. The connector is largely constituted by a fixed part which is connected to the sheathing tube, and a rotating part which is connected to the flexible shaft through an internal space of the fixed part. The probe controller is provided with a rotational shaft to be disconnectibly coupled with the rotating part of the connector, along with a retaining member which is located around the rotational shaft for fixedly holding the fixed part of the connector. A cable which is passed through the flexible shaft is electrically connected to the probe controller through electrode members provided in the rotating part. Accordingly, upon coupling the rotating part of the connector with the rotational shaft on the part of the probe controller, the electrodes of the rotating part are electrically connected with corresponding electrodes on the side of the rotational shaft.

The ultrasound scanner assembly at the distal end of the flexible cord of the probe has an ultrasound transducer element rotatably mounted within an end cap which connected to the sheathing tube of the flexible cord. The ultrasound element is supported on a rotary member which is connected to the fore end of the flexible transmission shaft. The end cap of the ultrasound scanner assembly is formed of a synthetic resin material having excellent properties in terms of acoustic characteristics, and its internal space is filled with an ultrasound transmission fluid medium. The end cap is securely fixed to the fore end of the flexible sheathing tube. The proximal end of the flexible cord is terminated with a tail end connector to be disconnectibly connected to the probe controller. The tail end connector is constituted by a ring-like stationary part which is connected to the sheathing tube, and a rotating part which is located within the fixed part and connected to the flexible transmission shaft. The stationary part of the tail end connector is fixedly connected to a stationary part of the probe controller, while the rotating part is rotationally coupled with a rotational drive means provided on the probe controller. A cable to or from the ultrasound transducer element is passed through the flexible transmission shaft and electrically connected with the probe controller through a pair of electrode members which are provided on the rotating part of the connector and which are connectible with corresponding electrode members on the part of the probe controller.

When the probe controller is operated to actuate the rotational drive of the rotational shaft, its rotation is transmitted to the flexible shaft through the rotating part of the connector, while the sheathing tube which is fitted on the flexible shaft is retained in a fixed state without rotating together with the flexible shaft. As will be understood from the foregoing description, in addition to the function of rotationally driving the flexible shaft, the probe controller functions as a signal relay means.

Since the outside diameter of the ultrasound probe is restricted by the inside diameter of an endoscopic biopsy channel on the endoscope, the ultrasound transducer element can only have an active surface of a limited size for transmission and reception of ultrasound signals. From the standpoint of permitting ultrasound scans of tissues in deep positions, it is desirable for the ultrasound transducer element to have as broad an active surface area as possible. In this connection, in the case of a front loading type ultrasound probe which is designed to be placed in an endoscopic biopsy channel from an inverse direction, that is to say, from the fore distal end of an endoscopic insertion instrument, it is possible to employ a bulky ultrasound scanner assembly with a large-size ultrasound transducer element because in this case there is no necessity of passing the ultrasound scanner assembly through the narrow endoscopic biopsy channel in a preparatory stage prior to introduction into a body cavity.

When an ultrasound probe is assembled into a biopsy channel of an endoscope, the ultrasound scanner head of the probe is projected to a certain extent from an exit opening of the biopsy channel at the distal end of the endoscopic insertion instrument. If an ensuing flexible cord portion is projected out of the endoscopic biopsy channel, letting the ultrasound scanner head hang down unstably like a pendant, there may arise difficulties in introducing the endoscopic insertion instrument smoothly into a body cavity or in locating the ultrasound scanner head precisely in an aimed position within the body cavity. Therefore, there must be provided some measures which can retain the ultrasound scanner head stably at the distal end of the endoscopic insertion instrument. In this regard, if the projected flexible cord portion is retracted into the endoscopic biopsy channel by pulling the probe in the rearward direction, the ultrasound scanner head which is larger than the inside diameter of the endoscopic biopsy channel can be fixedly held against marginal edges of the exit opening of the biopsy channel as long as the pulling force is applied to the probe.

The end cap which accommodates an ultrasound scanner head assembly is connected to a sheathing tube of the flexible cord portion of the probe normally by the use of a joint ring member of a diameter substantially same as or slightly larger than the inside diameter of the sheathing tube. Normally, a fore end portion of the sheathing tube is fitted on and bonded to the joint ring member which is projected from the side of the end cap. In some cases, for the purpose of augmenting the strength of the bonded joint portion, line wrapping is formed by winding a thread or filament around the outer periphery of the sheathing tube. The end cap, which is formed of a synthetic resin material for excellent properties in acoustic characteristics, can be easily deformed if directly connected with the sheathing tube of the flexible cord, resulting in separation from the latter. For this reason, it is the general practice to connect the end cap with the sheathing tube of the flexible cord through a connecting or joint member of rigid metallic material, fitting the sheathing tube on the connecting member over a substantial length.

The sheathing tube of the flexible cord is small in diameter and formed of a soft synthetic resin which is difficult to bond to the metallic connecting member with sufficient strength of adhesion by the use of an adhesive. Even if line wrapping is formed on the connected end of the sheathing tube in addition to an adhesive, it still has a possibility of being separated from the connecting member when an unduly large force is exerted thereon from outside. Therefore, when the flexible cord of the probe is forcibly pulled into the endoscopic biopsy channel for the purpose of holding the endoscopic scanner head fixedly against the fore end of the endoscopic insertion instrument as mentioned hereinbefore, the end cap of the scanner head can be caused to come off the sheathing tube of the flexible cord by a reaction force as it is pushed against the fore end of the endoscopic insertion instrument. The ultrasound scanner head can be fixed at the fore end of the endoscopic insertion instrument by providing a rubber ring or other stopper member around a flexible cord portion behind the ultrasound scanner head in such a way it functions as a stopper for the scanner head by frictional contact with inner surfaces of the endoscopic biopsy channel. Conversely, however, the provision of such stopper means makes it difficult to adjust the position of the ultrasound scanner head or to supply an ultrasound transmission fluid medium such as deaerated water into a body cavity through the endoscopic biopsy channel.

SUMMARY OF THE INVENTION

With the foregoing situations in view, it is an object of the present invention to provide an endoscopically inserting ultrasound probe with a stopper which is provided in a neck portion of the probe and which is arranged to hold an ultrasound scanner head fixedly at the distal end of an endoscopic insertion instrument in such a way as to keep the ultrasound scanner head from an external force which would act to separate the scanner head from a flexible cord portion of the probe.

It is another object of the present invention to provide a stopper mechanism for an endoscopically inserting ultrasound probe of the type having at the distal end of a thin flexible cord a bulky ultrasound scanner head larger in diameter than an endoscopic biopsy channel in which the ultrasound probe is to be placed, the stopper being adapted to hold the ultrasound scanner head fixedly and stably at the distal end of an endoscopic insertion instrument.

It is still another object of the present invention to provide a stopper for an endoscopically inserting ultrasound probe of the type as mentioned above, the stopper being adapted to hold the ultrasound scanner head fixedly and stably against marginal edges of a front opening of the biopsy channel at the distal end of an endoscopic insertion instrument upon pulling the flexible cord portion of the ultrasound probe into the endoscopic biopsy channel while keeping the ultrasound scanner head free from the pulling force applied on the flexible cord of the probe.

In accordance with the present invention, for achieving the abovestated objectives, there is provided an endoscopically inserting ultrasound probe to be introduced into a body cavity through a biopsy channel provided internally of an insertion instrument of an endoscope, the ultrasound probe being of the type having a bulky ultrasound scanner head at the distal end of an elongated thin flexible cord and being placed in the endoscopic biopsy channel except the bulky scanner head when in use, the ultrasound probe comprising: a stopper protuberance radially projected from a connecting neck portion of the ultrasound probe immediately on the proximal side of the scanner head where the flexible cord of the ultrasound probe is connected to a connecting member axially extended from the ultrasound scanner head, the stopper protuberance being abutted against marginal edges of a front opening of the endoscopic biopsy channel at a distal end of the endoscopic insertion instrument prior to the scanner head when the flexible cord is pulled thereinto, thereby keeping the scanner head from undergoing loads which would be imposed thereon upon direct abutment against a distal end portion of the endoscopic insertion instrument.

The stopper protuberance can be arranged in various forms. For example, it may be projected from part of a connecting member which is extended rearward from the ultrasound scanner head and connected to a flexible cord member of the probe by fitting engagement therewith. It is essential that the stopper protuberance be projected radially outward to a diameter larger than that of the endoscopic biopsy channel in which the ultrasound probe is to be placed. The radially outermost part of the stopper protuberance may be formed either as part of an outer tube of the flexible cord portion or as part of the connecting member extended from the ultrasound scanner head. Alternatively, the stopper protuberance may be provided in the form of a wedge ring which is fitted on the outer tube of the flexible cord in the connecting neck portion of the probe, the wedge ring being provided with a forwardly diverging tapered surface on the inner peripheral side thereof to grip a fore end portion of the outer tube securely against the connecting member by wedge action in cooperation with a complementarily tapered surface provided on the circumference of the outer tube or connecting member.

The above and other objects, features and advantages of the present invention will become apparent from the following particular description of the invention, taken in conjunction with the accompanying drawings which show by way of example some preferred embodiments of the invention.

DESCRIPTION OF PREFERRED EMBODIMENTS

Figure 1:
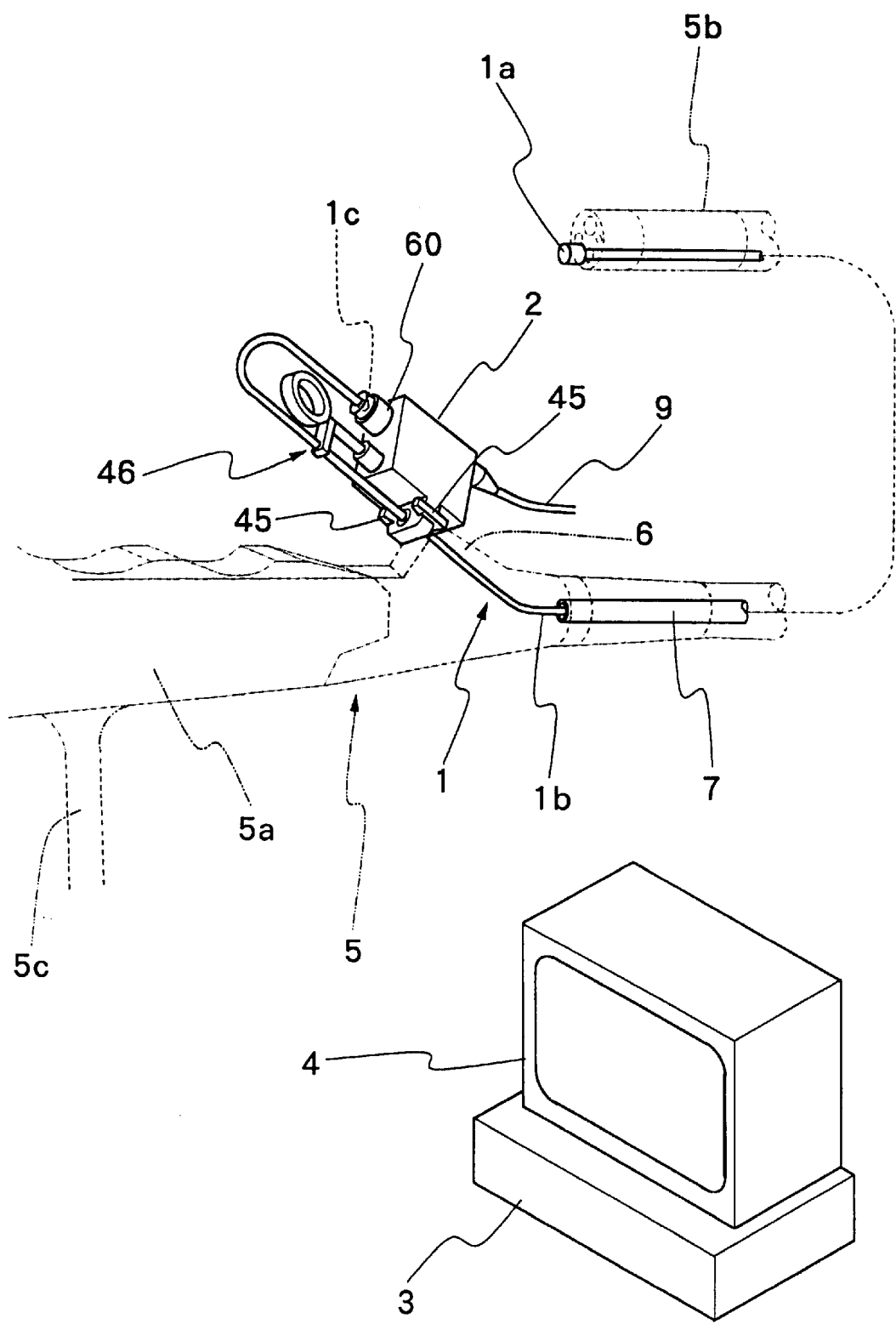
FIG. 1 is a schematic illustration of the general layout of an ultrasound examination system with an endoscopically inserting ultrasound probe.

Hereafter, the present invention is described more particularly by way of its preferred embodiments shown in the drawings. Schematically shown in FIG. 1 is the general layout of an ultrasound examination system incorporating an ultrasound probe coupling adaptor according to the present invention. The ultrasound examination system is largely composed of an ultrasound probe 1, a probe controller 2 and an ultrasound image observation terminal 3 with a monitor screen 4. The ultrasound probe 1 is of the type which is introduced into a body cavity by way of an endoscope 5, more specifically, by way of a biopsy channel 6 which is provided axially and internally of an endoscopic insertion instrument 5b and accessible through an entrance housing 6a, which is provided on a manipulating head grip 5a of the endoscope 5. Led out from the manipulating head grip 5a of the endoscope 5 is a universal cable 5c to be connected to a light source and an ultrasound signal processor which are not shown in the drawings.

Figure 2:
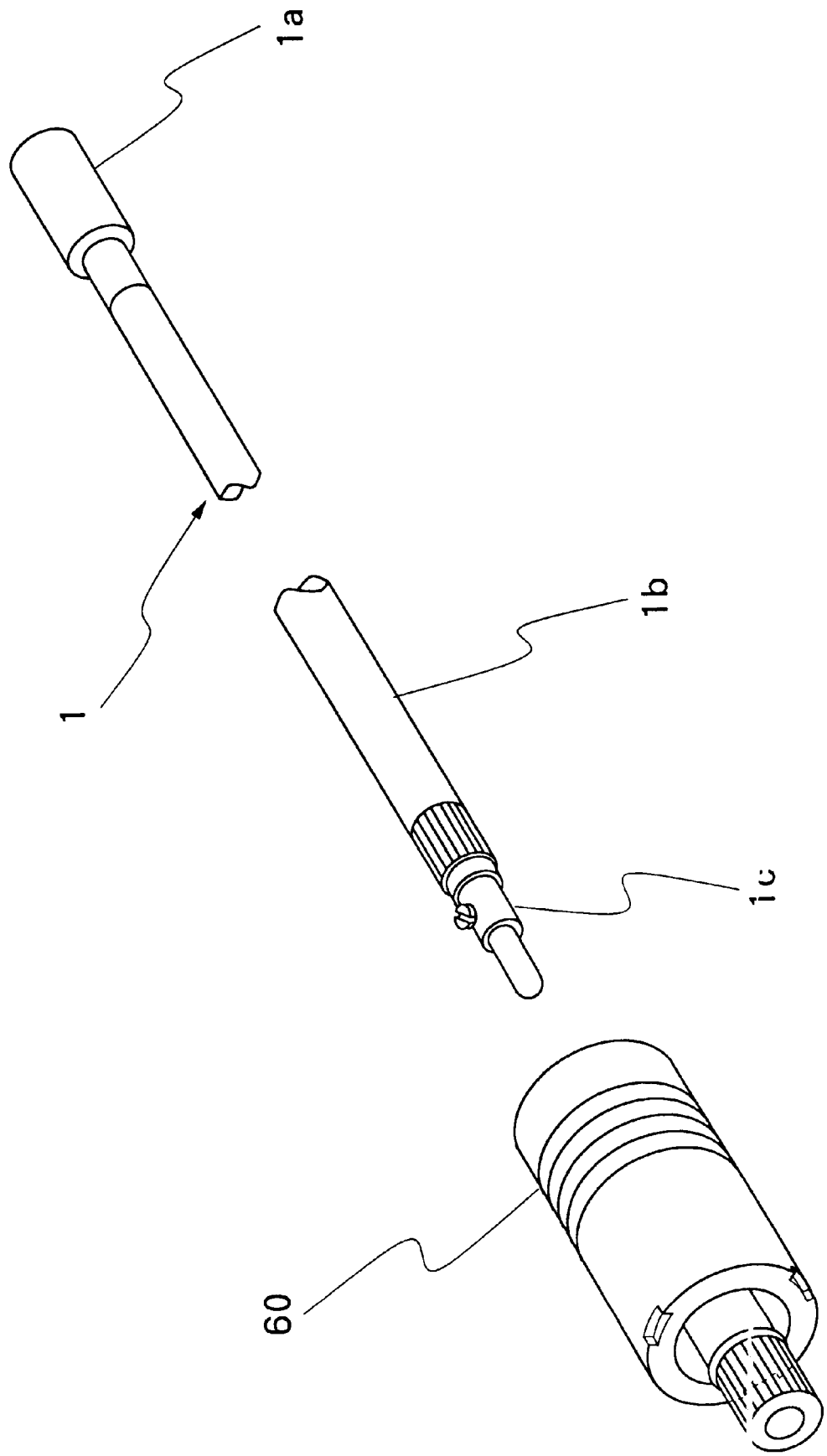
FIG. 2 is a fragmentary schematic view of an ultrasound probe and a coupling adaptor.
Figure 3:
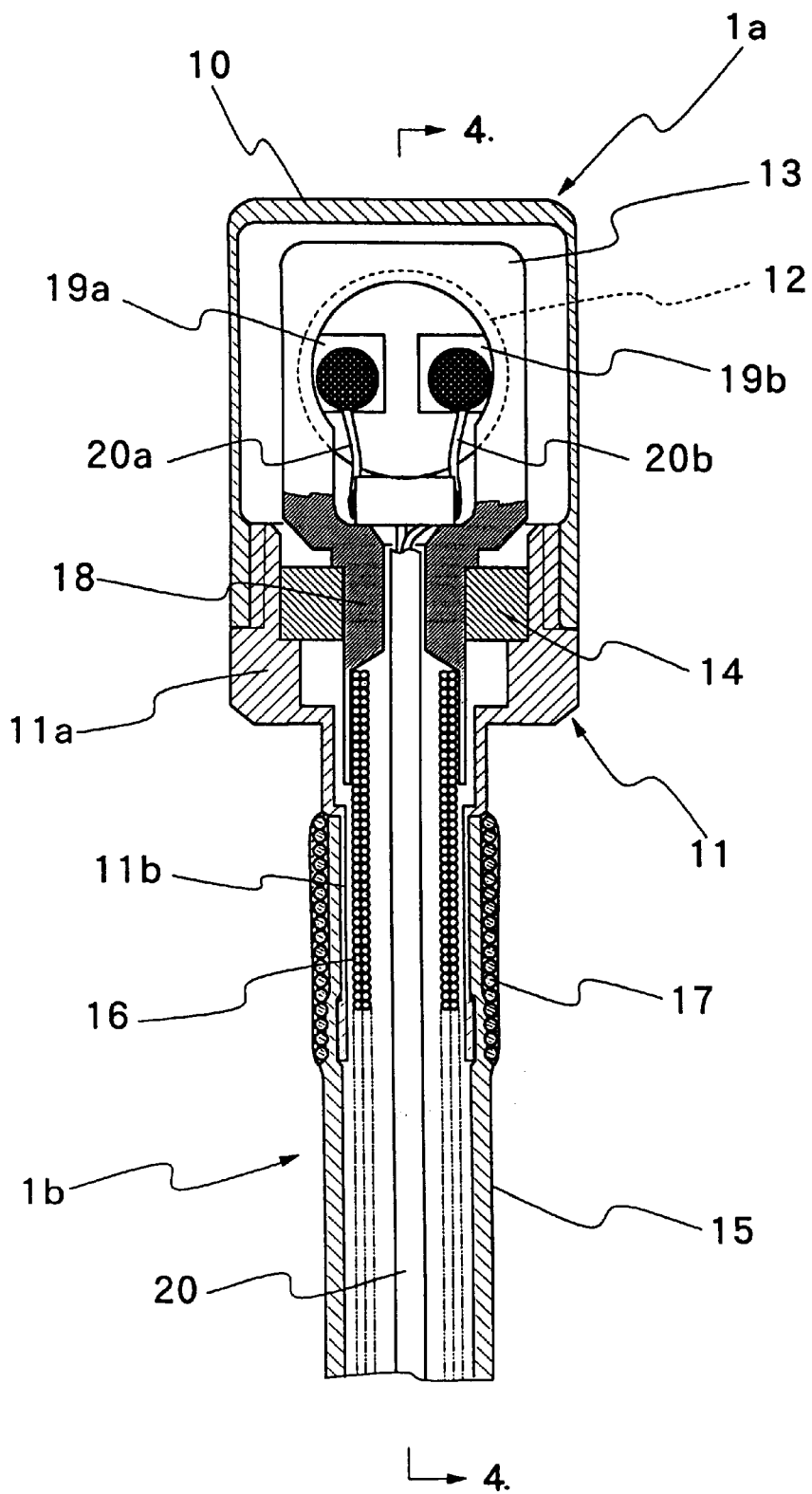
FIG. 3 is a fragmentary longitudinal section of a fore end portion of the ultrasound probe, with a stopper mechanism omitted for the sake of illustration of the ultrasound probe itself.
Figure 4:
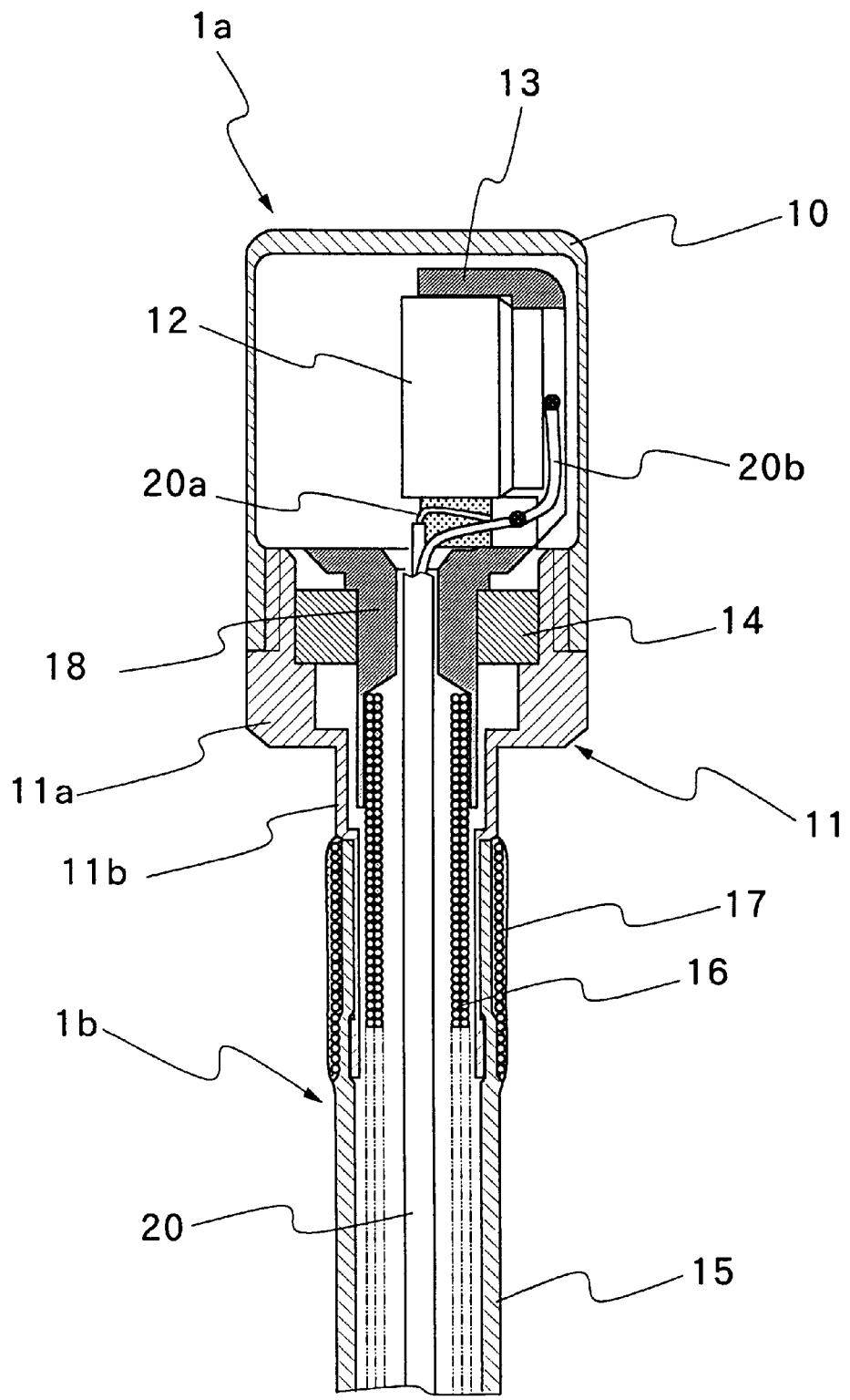
FIG. 4 is a longitudinal sectional view taken on line 4—4 of FIG. 3.

The ultrasound probe 1 as a whole is constructed as shown in FIG. 2. More specifically, as seen in FIG. 2, the ultrasound probe 1 is largely constituted by an ultrasound scanner head assembly 1a, a flexible cord 1b and a tail end connector 1c. As shown particularly in FIGS. 3 and 4, the ultrasound scanner head 1a is provided with an end cap 10 on a connecting member 11 which is formed of a rigid metallic material and provided with a large diameter portion 11a and a small diameter portion 11b. The ultrasound transducer element 13 is accommodated in the end cap 10, and mounted on a rotary member 14 which is rotatably supported within the end cap 10 through a bearing 14 to scan the ultrasound transducer element 12 in the radial direction. For accommodating a large-size ultrasound transducer element with a broad active surface area which can transmit strong ultrasound signals, the end cap 10 is of a bulky size having an outside diameter as larger than the inside diameter of the endoscopic biopsy channel 7 as possible within a range which would not obstruct the view field of endoscopic observation.

The flexible cord 1b is constituted by a flexible outer tube 15 of soft synthetic resin material or the like, and a flexible rotation transmission shaft 16 which is fitted in the outer tube 15. Fixedly connected to the fore distal end of the outer tube 15 is the connecting member 11 which is in turn fixedly connected to the end cap 10. The flexible transmission shaft 16 is constituted, for example, by tightly wound coils, preferably, by double layers of tightly wound coils of metal wires for transmitting rotations accurately in a reliable manner. The fore end of the outer tube 15 is fitted on the small diameter portion 11b of the connector member 11 and securely fastened to the latter by line wrapping 17, thereby fixedly connecting the end cap 10 at the fore end of the flexible cord 1b. The fore distal end of the flexible shaft 16 is securely fixed to a hollow rotary member 18 which is integrally connected to the rotary member 13. The ultrasound transducer element 12 is provided with a pair of electrodes 19a and 19b to connect signal lines 20a and 20b of a coaxial cable 20 which is passed through the neck member 18 and extended as far as the tail end connector 1c of the probe 1 through the internal space of the flexible shaft 16.

Figure 5:
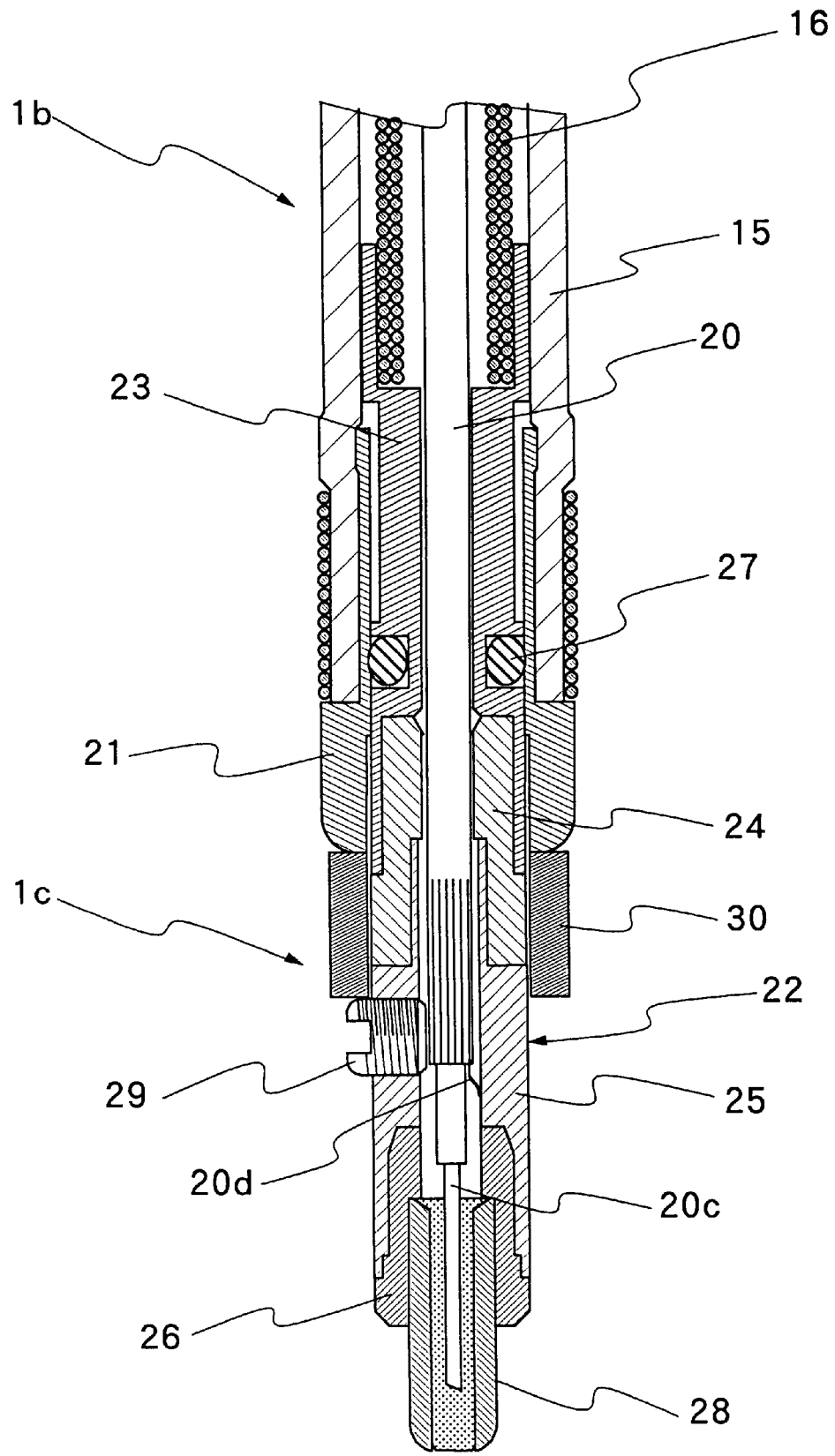
FIG. 5 is a longitudinal sectional view of a tail end portion of the ultrasound probe.

Shown on an enlarged scale in FIG. 5 is the probe construction where the proximal end of the flexible cord 1b is terminated with the tail end connector 1c. More specifically, the proximal end of the outer tube 15 is fixedly fitted on a tubular retainer shell 21 of metal. The proximal end of the flexible shaft 16 is connected to a rotational ring assembly 22 including an electrode ring. In this instance, the ring assembly 22 is composed of four rotary members or rings 23 to 26 which are successively threaded one in another in the axial direction. The first rotary ring 23 which is directly connected to the flexible shaft 16 is formed of a rigid metallic material with a sufficient degree of shape retainability and received in the retainer shell 21, which is similarly formed of a rigid metallic material, for sliding rotational movements therein. A seal member 27 is fitted on the first rotary ring 23 to seal off the clearance between the first rotary ring 23 and the retainer shell 21 air- and liquid-tight. Connected to the first rotary ring 23 is a second rotary ring 24 which is formed of an electrically insulating material such as a synthetic resin material or the like. A third rotary ring 25 which is connected to the second rotary ring 24 is formed of a metal or other conducting material, while a fourth rotary member 26 which is connected to the third rotary ring 25 is formed of an electrically insulating material.

In this case, for the purpose of ensuring the sealing capacity by the seal member 27, the first rotary ring 23 is formed of a metal or metallic material. The third rotary ring 25 is formed of a metal because it is required to function as an electrode to be connected to the ultrasound transducer element 12. Accordingly, the second and fourth rotary members 24 and 26 of electrically insulating material are located on the front and rear sides of the third rotary ring 25. The coaxial cable 20 is passed internally through the ring assembly 22, with its core wire 20c connected to a pin 28, which is fitted in the fourth rotary member 26, and its shield wire 20d connected to the third rotary ring 25.

Further, a rotation transmission pin 29 is securely planted in the third rotary ring 25. As described hereinbelow, the transmission pin 29 functions to transmit rotation to the ring assembly 22, and is arranged in such a way as to project radially outward from the outer periphery of the third rotary ring 25 by a predetermined length. A spacer ring 30 is fitted on the outer periphery of the ring assembly 22 between the rotation transmission pin 29 and the retainer shell 21. This spacer ring 30 is abutted against the front side of the rotation transmission pin 29 and rear end face of the retainer shell 21, thereby to retain the ring assembly 22, the flexible shaft 16 which is connected to the ring assembly 22, the flexible tube 16 and the retainer shell 21 in an inseparably assembled state. The spacer ring 30 is formed of an electrically insulating synthetic resin material or the like with suitable slipperiness. Thus, by the spacer ring 30, the retainer shell 21 is electrically insulated from the third rotary ring 25 and the rotation transmission pin 29 which are both formed of a metallic material.

Figure 6:
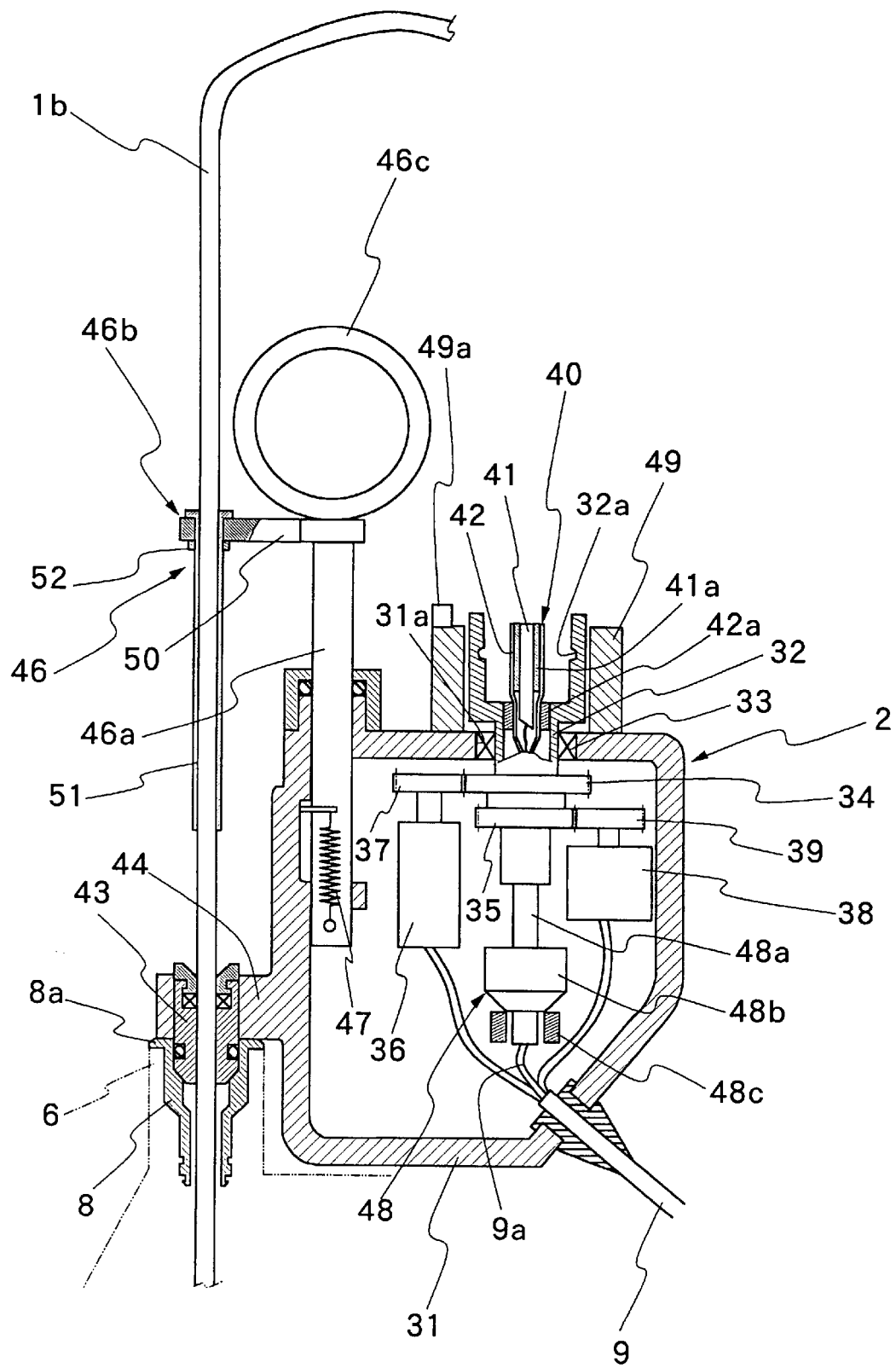
FIG. 6 is a schematic sectional view of a probe controller.

Referring now to FIG. 6, the probe controller 21 is provided with a casing 31 of an electrically insulating synthetic resin material or the like, in which a rotational shaft 32 is rotatably mounted through a bearing 33 to extend toward an opening 31a which is provided on the front side of the casing 31. Mounted on the rotational shaft 32 are a pair of gears 34 and 35. One gear 34 is meshed with a drive gear 37 which is mounted on an output shaft of an electric motor 36, while the other gear 35 is meshed with a follower gear 39 which is mounted on an input shaft of an encoder 38. Provided internally of the rotational shaft 32 is an electrode member 40 which is constituted by an inner pipe 41 and an outer pipe 42. These inner and outer pipes 41 and 42 are formed of an electrically conducting material and insulated from each other by an interposed insulating pipe 43. In addition, the outer pipe 42 is fitted in an insulating ring 44 which is fixedly fitted in the rotational shaft 32. Thus, by an adaptor 60 which will be described hereinbelow, the core and shield wires 20c and 20d of the coaxial cable 20 are electrically connected to the inner and outer pipes 41 and 42, respectively.

The probe controller 2 which is arranged in the above-described manner is removably attached on the entrance passage 6 of the biopsy channel 7, which is provided on the housing of the manipulating head grip 5a of the endoscope 5. For this purpose, a cylindrical connecting piece 43 is provided on an arm 44 which is projected outward from the casing 31 of the probe controller 2, and removably fitted in an opening 8 of the entrance passage 6 of the endoscopic head grip 5a. The arm 44 is provided with hooks 45 to be detachably engaged with a flange 8a portion which is formed around the entrance opening 8 of the endoscopic biopsy channel 7 (FIG. 1). The hooks 45 are urged to embrace the flange portion 8a by the action of springs, which are not shown in the drawings, thereby to hold the probe controller 2 of the ultrasound probe 1 fixedly on the head grip 5a of the endoscope 5.

As seen in FIG. 1, the tail end connector 1c and ensuing proximal end portion of the flexible cord 1b of the ultrasound probe 1 are led out of the endoscopic biopsy channel 7 through an axial passage in the connecting piece 43 which is fitted in the entrance housing 6, and connected to a tensioning means 46. The proximal end portion of the flexible cord 1b behind the tensioning means 46 is loosely looped and connected to the probe controller 2 through a coupling adaptor 60. The tensioning means 46 includes an operating rod 46a which is provided with a probe clamp member 46b.

Figure 7:
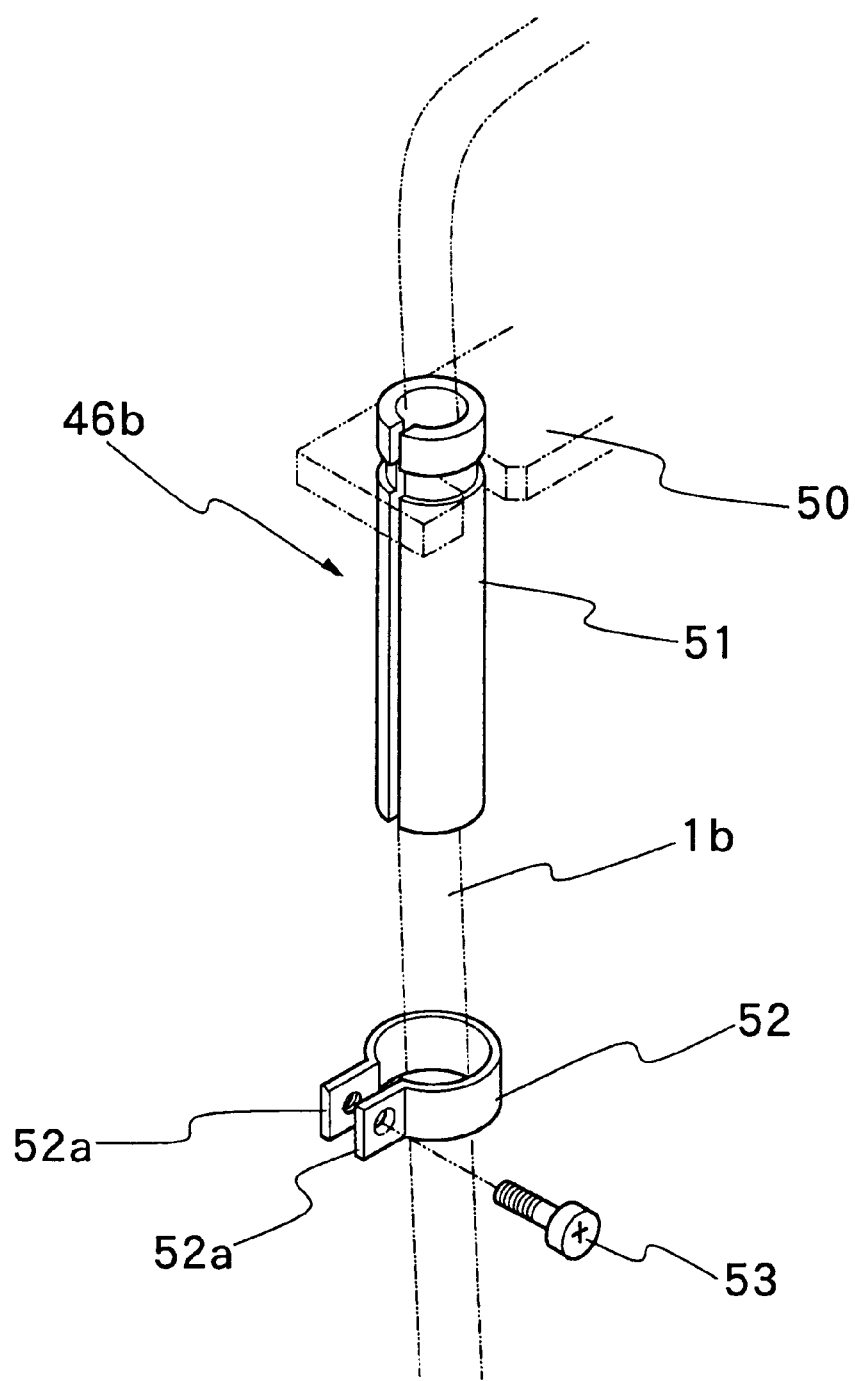
FIG. 7 is a schematic view of a probe clamper.

As clear from FIG. 7, the probe clamp member 46b is comprised of an arm 50 which is extended from the operating rod 46a, and an axially split holder pipe 51 which is gripped in a fore end portion of the arm 50. In turn, the flexible cord 1b coming out of the endoscopic biopsy channel 7 is passed through and releasably gripped in the holder pipe 51. Fitted on the holder pipe 51 is a clamp ring 52 which has flat clasp portions 52a at its opposite ends releasably fastened to each other by a screw 53. It follows that a proximal end portion of the flexible cord 1b of the ultrasound probe 1, outside the endoscopic biopsy channel 7, can be fixedly clamped by the clamp member 46b at an arbitrary position. The operating rod 46a is retractably mounted on the casing 31 of the probe controller 2, and constantly urged to protrude in the outward direction by the action of a spring 47 which is provided within the casing 31. The operating rod 46a can be pushed into and out of the casing 31 by way of a finger ring 46c which is provided at its outer end. Accordingly, when a proximal end portion of the flexible cord 1b is fixedly clamped by the clamp member 46b, the ultrasound probe 1 as a whole is constantly urged to retract toward the proximal end of the endoscopic biopsy channel 7 under the influence of the biasing action of the spring 47.

One end of the rotational shaft 32 is disposed in the opening 31a on the front side of the casing 31 as mentioned hereinbefore, while the other end of the rotational shaft 32 is connected to a rotary member 48a of a rotary connector 48 which is provided within the casing 31. A cable 9a from the to cable assembly 9 is connected to a stationary member 48b of the rotary connector 48. Further, the stationary member 48b of the rotary connector 48 is fitted in a rotation blocking member 48c and thereby blocked against rotational movements with the rotary member and at the same time prevented from twisting or torsional deformations. A cylindrical connection housing 49 is erected a round the opening 31a of the housing 31 in such a way as to circumvent the rotational shaft 32.

Figure 8:
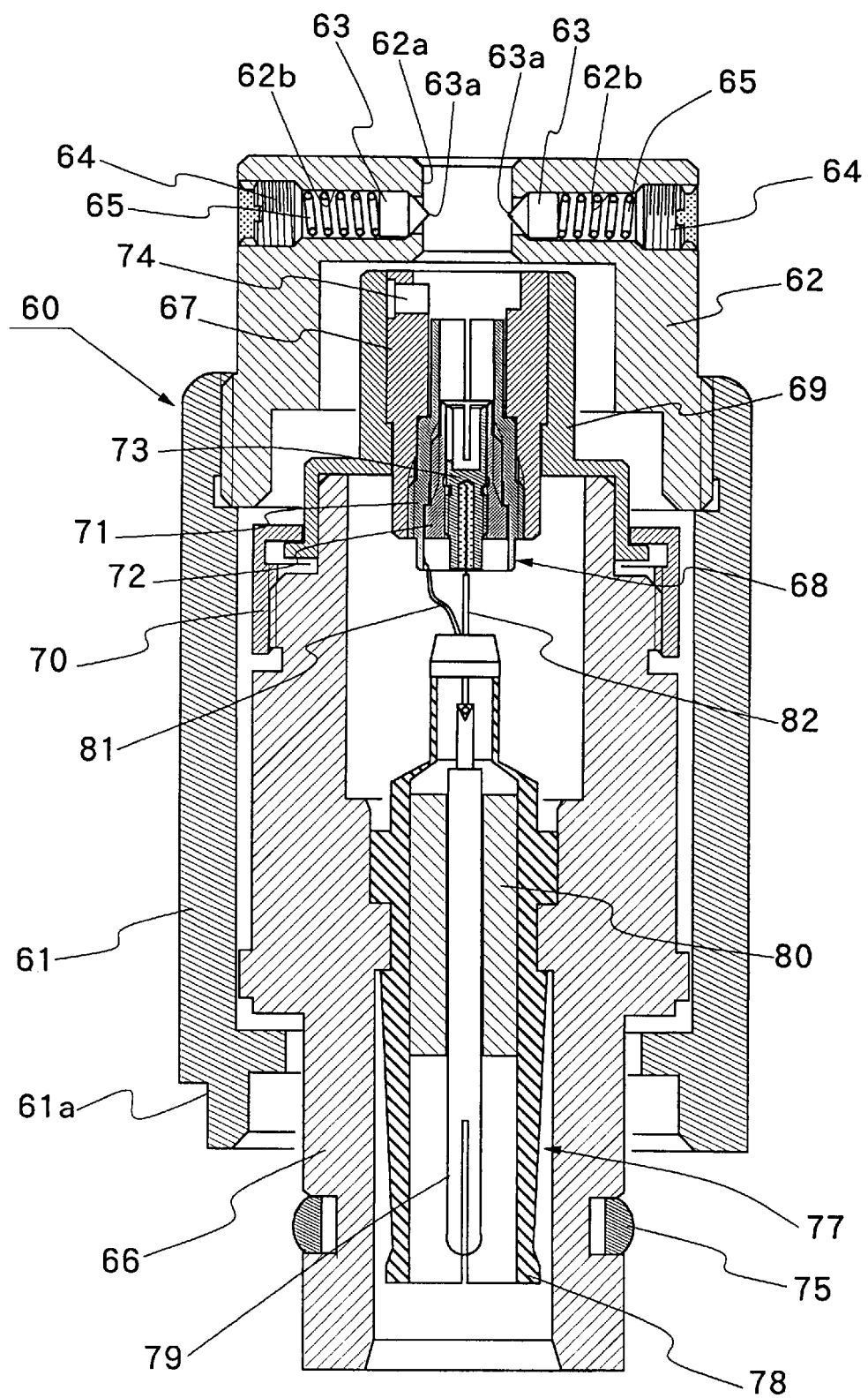
FIG. 8 is a longitudinal sectional view of the coupling adaptor.

The tail end connector 1c of the ultrasound probe 1 is coupled with the above-described probe controller 2 not directly but through a coupling adapt or 60 as described below. The coupling adaptor 60 is provided with a first or front coupling mechanism at one end to be connected to the tail end connector 1c of the probe and a second or rear coupling mechanism at the other end to be connected to the probe controller 2. More specifically, as shown particularly in FIG. 8, the coupling adaptor 60 is provided with stationary members including an outer housing 61 of substantially cylindrical shape and a retainer cap 62 which is threaded into one end of the outer housing 61. These stationary members of the adaptor are securely fixable relative to the casing 31 of the probe controller 2. To this end, the outer housing 61 is provided with a stopper groove 61a which is engaged with a stopper projection 49a on the part of the connection housing 49 of the probe controller 2 to block relative rotations of the fixed member of the adaptor 60 when connected to the latter. Further, the retainer cap 52 of the adaptor 60 is provided with an axial hole 62a to receive the retainer shell 21 of the tail end connector 1c of the probe 1. The retainer cap 62 is provided with a plural number of radial through holes 62b in its front end wall across the axial hole 62a to receive fixing screws 63, which are retractably protrudable into the axial hole 62a. More specifically, the fixing screws 63 are urged into the protruding positions by biasing springs 65 which are charged between the respective fixing screws 63 and spring seats 64. The fixing screws 63 are pointed at the respective inner ends for engagement in axial grooves (not shown) which are provided on the outer peripheral surface of the retainer shell 21 of the tail end connector 1c as rotation blocking grooves. When tail end connector 1c is inserted into the axial hole 62a of the retainer cap 62 up to the retainer shell 21, the pointed ends of the fixing screws 63 are engaged with the stopper grooves to block rotations of the retainer shell 21 and the outer tube 16 of the probe 1 during radial ultrasound scans when the ultrasound transducer element 13 is rotated through the flexible shaft 17.

The coupling adaptor 60 is further provided with rotary members internally of its stationary members including the housing 61 and the retainer cap 62. Major rotary members are rear and front rotary members 66 and 67 of generally hollow cylindrical shapes. A socket assembly 68 is threaded into the front rotary member 67 to receive the tail end connector 1c of the ultrasound probe 1 therein. The front rotary member 67 itself is threaded into a retainer ring 69 which is fixedly connected to the rear rotary member 66 by a box nut 70. A first tubular electrode pin 71 of the socket assembly is threaded into the front rotary member 67, which is formed of an electrically insulating material. A tubular insulating member 72 is threaded into the first tubular electrode pin 71, and a second tubular electrode pin 73 is fitted in this tubular insulating member 72. The first and second electrode pins 71 and 73 are in the form of axially split pins with spring characteristics. Further, a radial drive pin 74 is provided on the front rotary member 67, the drive pin 74 being abutted against the rotation transmission pin 29 on the part of the tail end connector 1c of the ultrasound probe 1 when the latter is connected to the coupling adaptor 60. By abutting engagement of the drive pin 74 with the rotation transmission pin 29, rotation is transmitted from the rotary members of the coupling adaptor 60 to the ring assembly 22 on the tail end connector 1c. Thus, an interlocked rotation transmission mechanism is constituted by the drive pin 74 and the transmission pin 29.

On the other hand, a C-ring 75 is fitted on a proximal end portion of the rear rotary member 66, the C-ring 75 being engageable with an annular groove 32a around the inner periphery of a larger-diameter coupling portion, which is provided at the outer or front end of the rotational shaft 32, for retaining the adaptor 60 securely in the connected position relative to the probe controller 2, precluding the possibilities of its dislocations. Further, the distal end portion of the rear rotary member 66, on the proximal side of the C-ring, is formed in a spline profile for engagement in the inner periphery 32b of an outer end portion of the rotational shaft 32 which is formed in a corresponding spline profile. Indicated at 77 is a connector member which is fixedly provided within the rear rotary member 66. This connector member 77 is constituted by a tubular outer cover 78 and an electrode rod 79, each formed of a conducting material. An insulating ring 80 is interposed between the outer cover 78 and the electrode rod 79 which are connected to the first and second tubular electrodes 71 and 73 through wires 81 and 82, respectively. Both of the outer cover 78 and electrode rod 79 are in the form of an axially split tubular structure. The rotary and stationary members may be assembled together through a bearing. In this particular embodiment, the housing 61 and the rear rotary member 66 are retained in small gap relation with each other. In case the rear rotary member 66 is loosely fitted in the housing 61 in this manner, the connector member 77 can be easily and snugly fitted in the rotational shaft 32 as the housing 61 is brought into engagement with the connection housing 49 on the part of the probe controller 2.

With the probe coupling adaptor of the construction as described above, for the purpose of transmitting ultrasound signals of lower frequency and higher power, the ultrasound probe 1 can employ an ultrasound transducer element 13 of a large size having a broader active surface area within the end cap 10 of on the ultrasound scanner assembly which is much larger than the inside diameter of the biopsy channel 7 on the endoscope 5.

Figure 9:
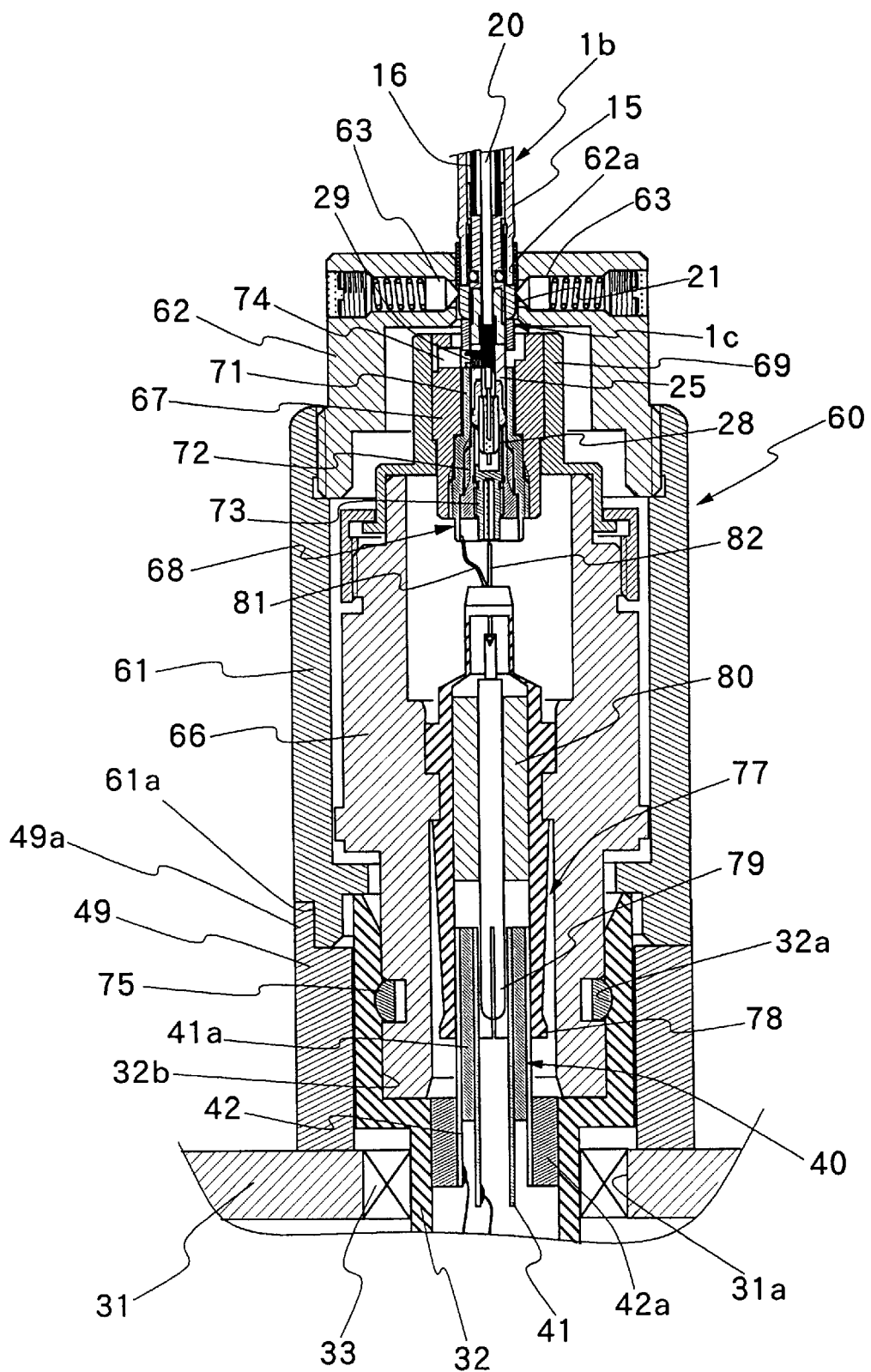
FIG. 9 is a schematic sectional view of the ultrasound probe which is coupled with the probe controller through the coupling adaptor.

In a preparatory stage prior to introduction into a body cavity of the insertion instrument 5b of the endoscope 5, the ultrasound probe 1 is placed in the endoscopic biopsy channel 7 through an opening at the distal end of the endoscopic insertion instrument 5b, drawing out the tail end connector 1c through the entrance way 6 on the manipulating head grip 5a of the endoscope 5. The proximal end portion of the flexible cord 1b, including the tail end connector 1c, which has been drawn out of the endoscopic biopsy channel 7 is threaded through the axial passage 43a in the connecting piece 43 on the probe controller 2. The flexible cord 1b is then clamped in the clamp member 46b of the tensioning means 46 at a suitable position before coupling the tail end connector 1c with the coupling adaptor 60. After this, the coupling adaptor 60 is connected to the probe controller 2. As a result, as shown in FIG. 9, the ultrasound probe 1 is electrically and rotationally coupled with the probe controller 2 through the coupling adaptor 60, permitting to rotationally drive the ultrasound transducer element 12 from the probe controller 2 and to transfer electrical signals between the ultrasound transducer element 12 and the ultrasound image observation terminal 3.

More specifically, upon connecting the rear rotary member 66 and housing 61 of the adaptor 60 with the rotational shaft 32 and connection housing 49 on the casing 31 of the probe controller 2, respectively, the connector member 77 is coupled with the electrode member 40 on the probe controller 2. Consequently, rotation of the rotational shaft 32 is transmitted to the ring assembly 22 of the ultrasound probe 2 through the rear and front rotary members 66 and 67 of the adaptor 60, and then to the flexible transmission shaft 16 which is connected with the rotating ring assembly 22. The signal lines 20a and 20b of the coaxial cable 20, to and from the ultrasound transducer element 13, are electrically connected with the first and second tubular electrodes 71 and 73 through the electrode pin 28 and the transmission pin 29, which are electrically connected with the inner and outer cover tubes 79 and 78 of the connector member 77 and the inner and outer pieces 41 and 42 of the electrode member 40 on the probe controller 2 through the wires 81 and 82, which are electrically connected with the ultrasound image observation terminal 3 through the rotary connector 48 and the cable 9.

In order to carry out an ultrasound scan or scans, after introducing the insertion instrument 5b of the endoscope into an intracavitary examination site, the ultrasound scanner assembly 1a which is projected from the distal end of the endoscopic insertion instrument 5b is abutted against an intracavitary wall. Then, the ultrasound transducer element 12 is put in rotation by remote control from the probe controller 2. At the same time the ultrasound transducer element 12 is driven to transmit ultrasound pulses into the patient's body at predetermined angular intervals, while converting received return echoes into electrical signals. At the ultrasound image observation terminal 3, the return echo signals from the ultrasound transducer element 12 are processed into video signals to display ultrasound images of body tissues on the monitor screen 4.

Thus, during a scanning operation, the ultrasound scanner head 1a of the probe 1 in the biopsy channel 7 of the endoscope 5 is projected from the distal end of the endoscopic insertion instrument 5b. However, if at this time part of the flexible cord 1b is also projected from the endoscopic insertion instrument 5b, it becomes extremely difficult to control the position of the ultrasound scanner head 1a, which is allowed to hang down unstably from the distal end of the endoscopic insertion instrument. This unstable state of the scanner head 1a makes it difficult not only to introduce the endoscopic insertion instrument smoothly into an intracavitary examination site but also to orient the ultrasound scanner head 1a toward an intracavitary region to be examined. Therefore, at the time of a scanning operation, the ultrasound scanner head 1a should be fixedly retained at the distal end of the endoscopic insertion instrument 5b substantially as an integral part of the latter. The fixation of the ultrasound scanner head 1a integrally at the distal end of the endoscopic insertion instrument 5b has great importance in consideration of the fact that the endoscope 5 is usually provided with an angle section in a fore end portion of its insertion instrument for angularly flexing the fore end of the insertion instrument toward a desired direction, permitting to turn the ultrasound scanner head 1a into the desired direction simultaneously with the flexing operation on the angle section of the endoscope 5.

For this purpose, the flexible cord 1b of the ultrasound probe 1 has constantly applied thereto a predetermined tensioning force by the tensioning means 46 which is provided on the probe controller 2, urging the flexible cord 1b to retract into the endoscopic biopsy channel 7. In order to apply a tension to the flexible cord 1b of the probe 1, the operating rod 46 is pushed into the casing 31 by way of the finger ring 46c before clamping a predetermined proximal end portion of the flexible cord 1b in the probe clamp member 46b. In this state, upon releasing the finger ring 46c, the operating rod 46a is pushed back into the outer projecting position by the action of the biasing spring 47, thereby applying to the flexible cord 1b a tensioning force acting to retract the flexible cord 1b into the endoscopic biopsy channel 7 until the ultrasound scanner head 1a is abutted against the distal end face of the endoscopic insertion instrument 5b. At this time, since the ultrasound scanner head assembly 1a is larger than the inside diameter of the endoscopic biopsy channel 7, it is pushed against marginal edge portions of the exit opening of the biopsy channel 7 and fixedly held against the distal end face of the endoscopic insertion instrument 5b.

However, if the ultrasound scanner head 1a is pushed directly against the distal end face of the endoscopic insertion instrument 5b, the ultrasound scanner head 1a can be subjected to a reaction force which acts in a direction of separating the scanner head 1a from the flexible cord 1b, with possibilities of breaking the adhesive bondage between the outer sheathing tube 15 and the connecting member 11 which is connected with the end cap 10 and causing separation of the connecting member 11 from the outer tube 15. In order to prevent problems of this sort, the ultrasound scanner head 1a should be kept from abutting contact with the distal end face of the endoscopic insertion instrument 5b.

The fore end of the outer sheathing tube 15 of the flexible cord 1b fitted over a predetermined length on the small-diameter neck portion 11b of the connecting member 11, which is in the form of a hollow cylinder of rigid metal. Therefore, this neck portion 11b in fitting engagement with the outer tube 15 provides a rigid portion which can be directly or indirectly abutted against marginal edges of the opening of the endoscopic biopsy channel 7 for the purpose of fixedly retaining the ultrasound scanner head 1a relative to the insertion instrument 5b of the endoscope 5, in such a way as to keep the ultrasound scanner head 1a free from the tensioning force or other external forces which act on the outer tube 15 of the flexible cord 1b. According to the present invention, this is achieved by providing a stopper mechanism in a neck portion of the ultrasound probe 1 where the small diameter portion at the base end of the ultrasound scanner head 1a fittingly connected with a fore end portion of the flexible cord 1b.

Figure 10:
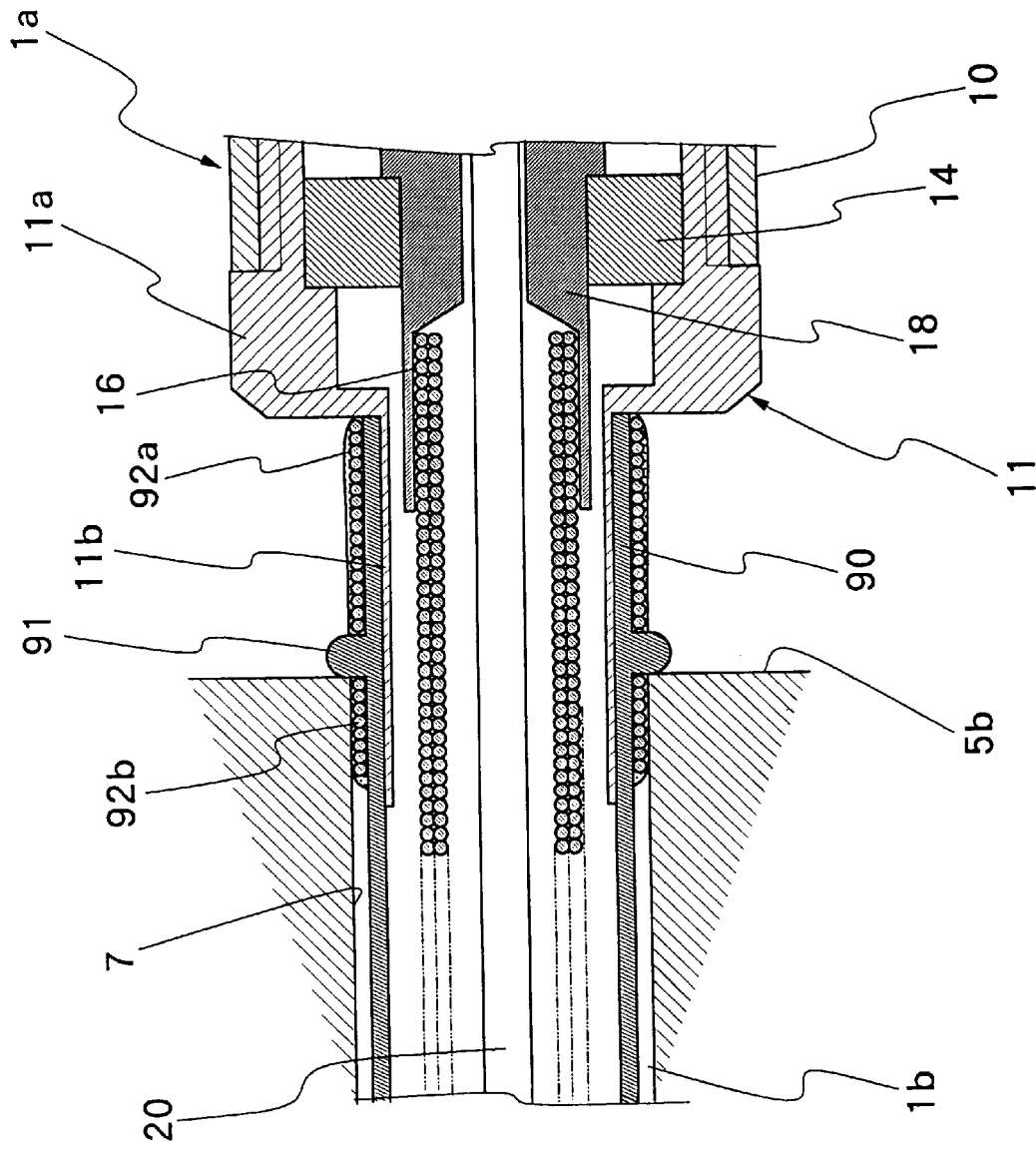
FIG. 10 is a schematic sectional view of a stopper protuberance which is provided in a neck portion of the ultrasound probe.

Shown in FIG. 10 is an example of a connecting neck portion with a stopper means provided on the flexible cord 1b. More specifically, in this particular embodiment, the flexible cord 1b of the probe 1 is formed with an annular protuberance 91 around its circumference in its fore end portion which is fitted on the connecting member 11 of the ultrasound scanner head assembly 1a. The annular protuberance 91 is radially projected to a diameter which is larger than the diameter of the opening of the biopsy channel 7 at the distal end of the endoscopic insertion instrument 5b, so that, when the outer sheathing tube 90 can be pulled into the endoscopic biopsy channel 7, it is stopped as soon as the annular protuberance 91 is abutted against edge portions around the opening of the endoscopic biopsy channel 7. The outer tube 90 itself is formed of a soft synthetic resin material. However, since outer tube 90 is fitted on and around the rigid connecting member 11, there is no possibility of the outer tube 90 being deformed into a different diameter at least in its fore end portion in engagement with the connecting member 11. Therefore, even if a strong tensile force is applied on the outer tube 90, the annular protuberance 91 can retain its diameter and can securely function as a stopper without undergoing contractions in diameter by deformation. This means that, when the flexible cord 1b of the ultrasound probe 1 is pulled inward of the endoscopic biopsy channel 7, no load is applied on the ultrasound scanner head 1a at the distal end of the flexible cord 1b.

Thus, thanks to the stopping functions of the annular protuberance 91 which keeps the ultrasound scanner head 1a from a pulling force which would otherwise tend to separate the scanner head 1a from the flexible cord 1b, the outer tube 90 can be securely connected to the connecting member 11 simply by the use of an adhesive. Nevertheless, the outer tube 90 may be more securely fastened to the connecting member 11 by forming line wrapping therearound. For this purpose, as shown in FIG. 10, it is desirable to form line wrapping around the outer tube 90 not only on the front side of the annular stopper protuberance 91 as indicated at 92a but also on the proximal side of the annular protuberance 91 as indicated at 92b. By these line wrappings, the outer tube 90 can be connected more strongly to the connecting member 11 while retaining the shape of the annular stopper protuberance 91 more stably against deformations which might otherwise be caused by external forces, to guarantee its functions as a stopper despite the resiliency and flexibility of the material which constitutes the annular protuberance 91.

Further, at the time of an ultrasound examination, there may arise the necessity of supplying an ultrasound transmitting fluid medium like deaerated water to an intracavitary examination site where the ultrasound scanner head 1a is located. In such a case, it is the general practice to supply deaerated water through the endoscopic biopsy channel 7. In order to open up the endoscopic biopsy channel 7 for this purpose, the operating rod 46a of the tensioning means 46 is pushed into the housing 31 of the probe controller 2, whereupon the flexible cord 1b of the probe 1 is pushed forward and projected out of the endoscopic biopsy channel 7, as a result causing the annular protuberance 91 on the outer tube 90 to disengage and move away from the front opening of the endoscopic biopsy channel 7, permitting to supply deaerated water through a gap space between the biopsy channel 7 and the flexible cord 1b. As soon as the operating rod 46a is put in a free state and allowed to return to the outwardly projected position, the annular protuberance 91 on the outer tube 90 is once again abutted against marginal edges of the opening at the distal end of the endoscopic biopsy channel to hold the ultrasound scanner head 1a fixed at the distal end of the endoscopic insertion instrument.

Figure 11:
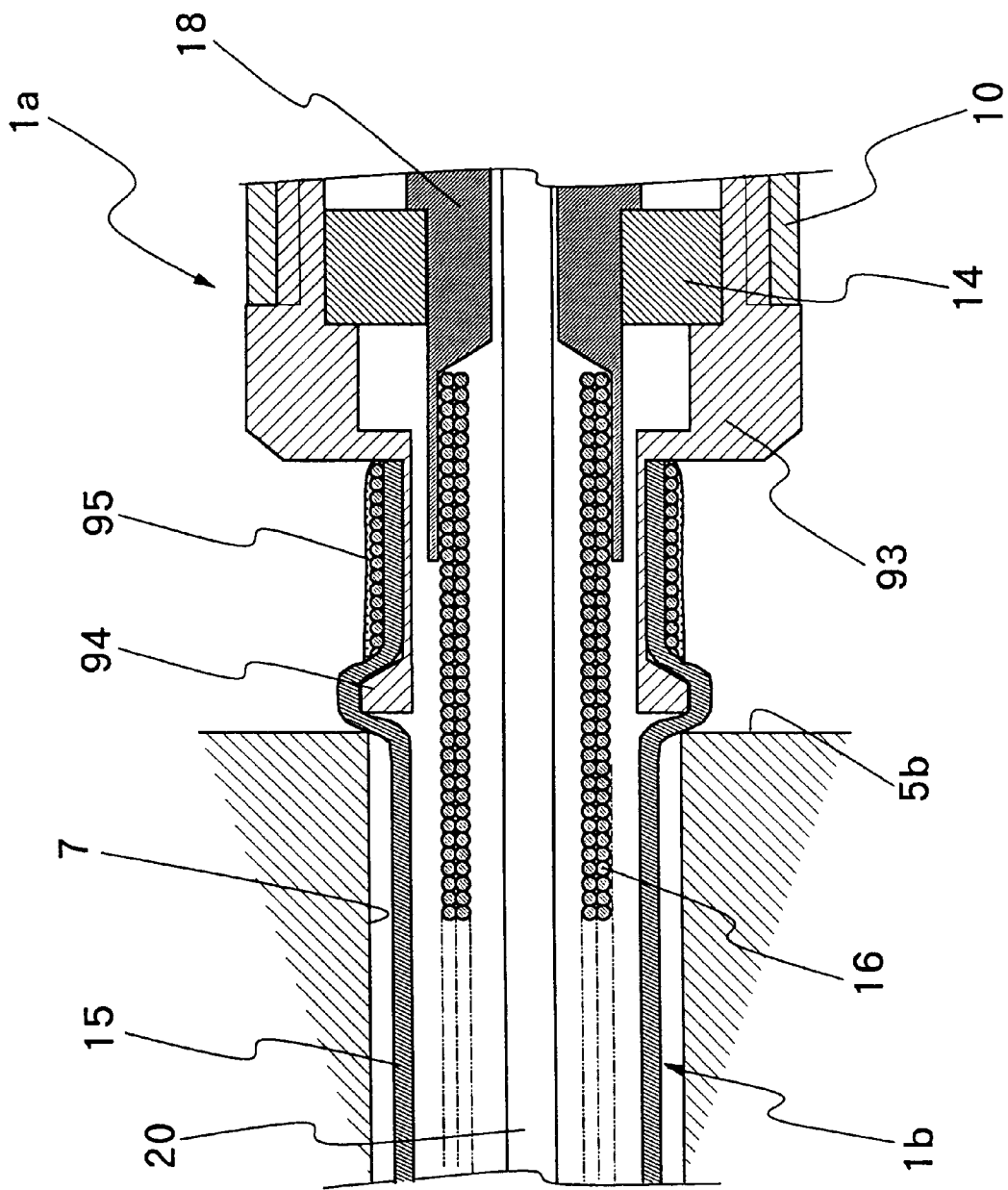
FIG. 11 is a schematic sectional view of a stopper protuberance of a modified form.

Referring now to FIG. 11, there is shown a second embodiment of the present invention. Although the thickness of the outer tube is partly increased in the embodiment of FIG. 10 to form an annular protuberance projecting radially outward from the circumference of the outer tube at the connecting neck portion of the probe, this embodiment employs an outer tube which has a substantially uniform wall thickness similarly to the outer tube 15 shown in FIGS. 3 and 4. Instead, in this case, an annular protuberance is provided around the proximal end of the connecting member 93. Since the outer tube 15 is formed of a soft and flexible synthetic resin material as mentioned hereinbefore, it can be easily deformed into a larger diameter when subjected to a forcible spreading force and can be fit along the contour of the annular protuberance 94 which projects radially outward from the circumference of the connecting member 93. Accordingly, the outer tube portion which fits around the annular protuberance 94 bulges out in the radially outward direction beyond the inside diameter of the endoscopic biopsy channel 7, forming a stopper protuberance which prevents the ultrasound scanner head 1a from being subjected to external forces which would act to separate the scanner head 1a and the flexible cord 1b from each other. The stopper protuberance which is formed by the annular protuberance 94 can also be separated from the endoscopic biopsy channel 7 by pushing a fore end portion of the flexible cord 1b out of the biopsy channel 7, if necessary for opening up a passage for deaerated water through the biopsy channel 7. In this instance, the outer tube 15 of the flexible cord 1b is securely bonded to the connecting member 93 by the use of an adhesive. However, similarly line wrapping 95 may be provided around the outer tube 15 on the front side of the annular protuberance 94. By this line wrapping 95, the connecting fore end portion of the outer tube 15 is more strongly fastened and connected to the connecting member 93.

Figure 12:
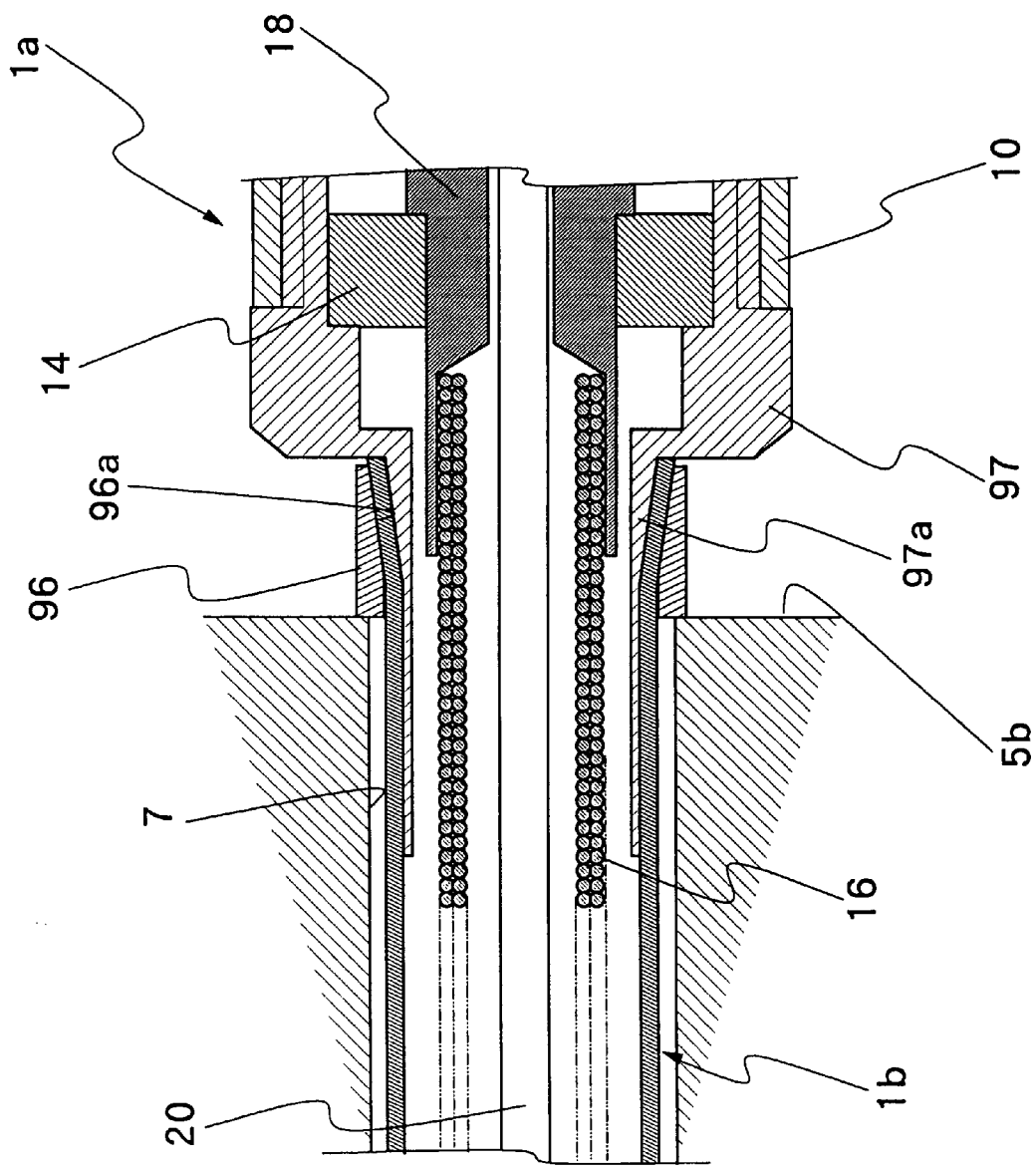
FIG. 12 is a schematic sectional view, showing another modification of the stopper protuberance.
Figure 13:
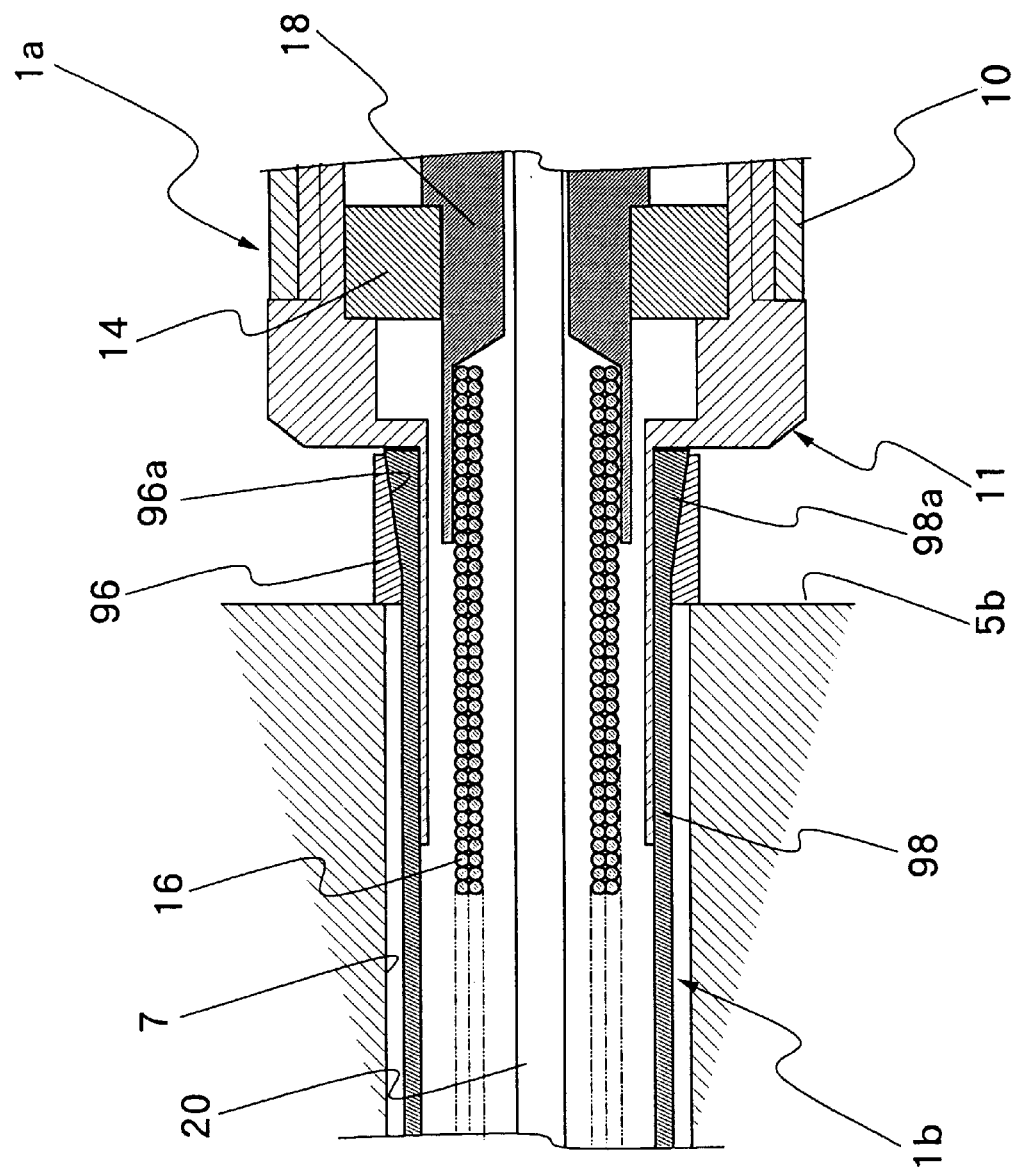
FIG. 13 is a schematic sectional view, showing still another modification of the stopper protuberance.

Illustrated in FIGS. 12 and 13 are further modifications employing a ring-like wedge member 96 as a stopper protuberance for keeping the ultrasound scanner head 1a from the tensile force which is applied to the flexible cord 1b of the probe 1.

The wedge member or wedge ring 96 which is fitted around a neck portion of the ultrasound probe 1 is provided with a forwardly diverging tapered surface 96a on the inner peripheral side, formed by thinning down its wall thickness continuously in such a way as to have an inside diameter gradually increasing in a direction toward its front end. The wedge ring 96 has an outside diameter which is larger than the inside diameter of the endoscopic biopsy channel 7. The wedge ring 96 is fitted in position on the connecting neck portion of the probe 1 with its tapered diverging end on the side of the ultrasound scanner head 1a.

In the modification shown in FIG. 12, for engagement with the tapered surface 96a on the wedge member or ring 96, a correspondingly or complementarily tapered surface 97a is formed on the art of the connecting member 97. Accordingly, as the ultrasound probe 1 is pulled into the endoscopic biopsy channel 7, the fore end of the tube 15 is gripped between the tapered surfaces 96a and 97a of the wedge ring 96 and connecting member 97. In this case, the greater the pulling force, the stronger becomes the gripping force on the tube 15 to prevent separation of the ultrasound scanner head 1a from the flexible cord 1b.

Alternatively, a tapered surface may be formed on the side of a tube 98 for engagement the tapered surface 96a of the wedge ring 96 as shown in FIG. 13. In this case, a complementarily tapered surface 98a is formed by gradually increasing the outside diameter or the wall thickness of the tube 98 toward its fore end. In this case, the fore end of the tube 98 is wedged on the small diameter portion 11b immediately on the proximal side of the large diameter portion 11a of the connecting member 11 to keep the ultrasound scanner head 1a from a pulling force which would otherwise act to separate the scanner head 1a from the outer tube 98 of the flexible cord 1b.

In this instance, the rear end face of the wedge member 96 is brought into abutting engagement with marginal edge portions around the front opening of the endoscopic biopsy channel 7. Therefore, the wedge member 96 can be separated away from the endoscopic biopsy channel 7 upon pushing the flexible cord 1b forward of the endoscopic biopsy channel 7 when it becomes necessary to open up the biopsy channel to use it as a deaerated water feed passage or for other purposes.

What is claimed is:

1. An endoscopically insertable ultrasound to be introduced into a body cavity through a biopsy channel provided internally of an insertion instrument of an endoscope, said ultrasound probe having a bulky scanner head which has a diameter larger than said biopsy channel, and a flexible cord and a tail end connector both of which have diameters smaller than said biopsy channel, said ultrasound probe comprising:

a stopper protuberance radially projected from a connecting neck portion of said ultrasound probe immediately on the proximal side of said scanner head where said flexible cord of said ultrasound probe is connected to a connecting member axially extended from said ultrasound scanner head, said stopper protuberance being adapted to be abutted against marginal edges of a front opening of said endoscopic biopsy channel at a distal end of said endoscopic insertion instrument to keep said scanner head apart from said marginal edges, so as to maintain said scanner head free from loads being applied thereto when said flexible cord is pulled into said biopsy channel in order to hold said scanner in a stable position.

2. An endoscopically inserting ultrasound probe as defined in claim 1, wherein said stopper protuberance is projected radially outward from and outer periphery of said flexible cord to a diameter larger than inside diameter of said endoscopic biopsy channel.

3. An endoscopically inserting ultrasound probe as defined in claim 2, wherein said stopper protuberance is in the form of an annular protuberance formed around the outer periphery of said flexible cord in said connecting neck portion of said probe.

4. An endoscopically inserting ultrasound probe as defined in claim 1, wherein said stopper protuberance comprises by an annular protuberance formed around a cylindrical connecting portion of said scanner head and a fore end portion of a sheathing outer tube of said flexible cord forcibly fitted on said annular protuberance and bulging out in the radial direction to a diameter larger than inside diameter of said endoscopic biopsy channel.

5. An endoscopically inserting ultrasound probe as defined in claim 1, wherein said stopper protuberance comprises by a wedge ring fitted on said flexible cord in said connecting neck portion of said ultrasound probe, said wedge ring being provided with a forwardly diverging tapered surface on the inner peripheral side thereof to grip a fore end portion of an outer sheathing tube of said flexible cord firmly by wedge-like action in cooperation with a complementarily tapered surface formed either on said outer sheathing tube or on said connecting member of said ultrasound scanner head.

* * * * *

UNITED STATES PATENT AND TRADEMARK OFFICE
CERTIFICATE OF CORRECTION

PATENT NO. : 5,971,929

DATED : October 26, 1999

INVENTOR(S): Toshio SAKAMOTO, et al.

It is certified that an error appears in the above-identified patent and that said Letters Patent is hereby corrected as shown below:

On the title page, item [30] has been omitted. It should be:

--[30]     Foreign Application Priority Data
    Sep. 16, 1997   [JP]   Japan  ........... 9-268215--

Signed and Sealed this

Eleventh Day of July, 2000

Attest:

Q. TODD DICKINSON

*Attesting Officer*     *Director of Patents and Trademarks*